United States Patent

Poler

Patent Number: 5,618,292
Date of Patent: Apr. 8, 1997

[54] CORNEAL DRAPE OR TEMPLATE FOR PERFORMING A RADIAL-KERATOTOMY PROCEDURE

[76] Inventor: Stanley Poler, 78 E. Second St., New York, N.Y. 10003

[21] Appl. No.: 397,573

[22] Filed: Mar. 2, 1995

Related U.S. Application Data

[63] Continuation of Ser. No. 205,894, Mar. 2, 1994, abandoned.

[51] Int. Cl.⁶ .................................................. A61B 17/00
[52] U.S. Cl. ............................................ 606/166; 33/512
[58] Field of Search ............................ 606/1, 108, 166, 606/167, 172; 30/114; 33/507, 511, 512, 566

[56] References Cited

U.S. PATENT DOCUMENTS

| | | |
|---|---|---|
| 4,340,059 | 7/1982 | Marinoff. |
| 4,406,285 | 9/1983 | Villasenor et al. |
| 4,520,815 | 6/1985 | Marinoff .......................... 606/166 |
| 4,648,400 | 3/1987 | Schneider et al. |
| 4,688,570 | 8/1987 | Kramer et al. ..................... 606/166 |
| 4,705,037 | 11/1987 | Peyman et al. |

FOREIGN PATENT DOCUMENTS

| 1335282 | 9/1987 | U.S.S.R. ........................... 606/166 |

*Primary Examiner*—Michael Powell Buiz
*Assistant Examiner*—William Lewis
*Attorney, Agent, or Firm*—Hopgood, Calimafde, Kalil & Judlowe

[57] ABSTRACT

A template of flexible material that is so fenestrated or otherwise configured as to be self-adherent to the cornea and to readily conform to the curvature of the cornea, the template being further configured to provide ready centering on the visual axis and to establish a removable pattern of knife-guiding slits, wherein the pattern is selected as a particular one, from a plurality of available patterns, each of which has been designed to serve a different but predetermined optical change via an RK and/or an AK procedure. The self-adherence is relative, intended only to serve correctly guided use of a knife, in that the template is readily removable after the intended cuts have been made. A variety of embodiments is disclosed.

31 Claims, 4 Drawing Sheets

CORNEAL DRAPE OR TEMPLATE FOR PERFORMING A RADIAL-KERATOTOMY PROCEDURE

This application is a continuation of Ser. No. 08/205,894, filed Mar. 02/1994, now abandoned.

BACKGROUND OF THE INVENTION

The invention relates to the performance of surgery upon the anterior surface of the cornea, in order to change the anterior-surface profile and thereby change the optical performance of a given eye, via in vivo surgery.

Radial keratotomy (RK) is the term currently used to describe such a procedure, for the case of plural slits cut at spaced locations about the optical axis of the eye, and cut to a depth that is (a) less than the thickness of the cornea and (b) in an annular region which is outside the optical zone, i.e., outside the optically used central region of the cornea. The result is to circumferentially weaken and thus to allow the front-surface curvature of the optically used region to flatten, in reduction of a myopic condition or in reduction of an astigmatic condition (AK), depending upon the symmetry of cut distribution, or upon the orientation of the asymmetry of cut distribution, as the case may be.

To date, an accumulation of data and experience exists from which to enable the ophthalmic surgeon to predict, with some degree of reasonable approximation, the number, the depth, and the distribution of cuts to be made in order to approximate a desired optical correction, to the extent that the patient quickly is aware of an improvement in his eyesight, following RK surgery. And suppliers of ophthalmic tools and instruments have refined their offerings in recognition of the need for precision in what remains essentially a manual operation. For example, Katena Products, Inc. of Denville, N.J., devotes a double-page spread in its current catalog, "Katena Diamond Knives", to the listing, diagramming and description of six different kinds of diamond micrometer knives, specifically for use in RK surgery and/or AK (astigmatic keratotomy) surgery. Each knife is equipped with a footplate for sliding reference to the corneal epithelium in the course of making a cut, and a micrometer scale is associated with axial-displacement mechanism in the knife handle to enable precise setting of the extent to which the cutting end of the knife is to project beyond the front surface of the footplate. Such settings are adjustable in 10-micron increments, from 0 to 1.5-mm, and a special gauge enables the surgeon to double-check whether the setting is precisely what was intended via the micrometer adjustment.

However, with all the precision and quality of cut that can be made with such a fine knife instrument, the fact remains that it is the surgeon upon whom ultimate reliance must be placed, because radial and astigmatic surgical procedures continue to be hand operations.

Among the further currently available instrumentation in aid of RK and AK keratotomies are the various marking instruments whereby to mark the patient's cornea, in identification of one or more features, including the visual-axis intercept, the optically used central area (i.e., the optic zone), a T-incision marker with a succession of blade-length offerings, an astigmatism marker, a helicoidal marker, and a hexagon open-pattern marker. These and other marker products are shown in another Katena Products catalog, "Instruments for Radial and Astigmatic Keratoplasty". Again, however well the cornea may have been marked for surgery, the fact remains that the final quality of a given operation rests entirely on the manual skill of the ophthalmic surgeon, in that all marker instruments must be out of the way while the manual operation proceeds.

BRIEF STATEMENT OF THE INVENTION

It is an object of the invention to provide means whereby surgery of the character indicated may be performed with greater accuracy and precision than heretofore.

Another object is to meet the above object with means whereby a surgeon having less than the greatest manual dexterity and operative skills may perform an RK and/or an AK procedure with predictably greater precision than has been previously obtainable.

A specific object is to provide a template (a) which will flexibly conform to the curvature of the cornea, and b) which will sufficiently adhere to the eye to permit its function as a surgical guide throughout an RK and/or an AK procedure. Another specific object is to provide a template meeting the above specific object and capable of controlling a predetermined profile of varying depth of cut. Still another specific object is to meet the above specific objects with a template having tactile or visual indicia which can be sensed by the surgeon in the course of making a particular cutting pass in the performance of his surgical procedure.

The invention achieves the foregoing objects by providing a template of flexible material that is so fenestrated or otherwise configured as to be self-adherent to the cornea and to readily conform to the curvature of the cornea, the template being further configured to provide ready centering on the visual axis and to establish a removable pattern of knife-guiding slits, wherein the pattern is selected as a particular one, from a plurality of available patterns, each of which has been designed to serve a different but predetermined optical change via an RK and/or an AK procedure. The self-adherence is relative, intended only to serve correctly guided use of a knife, in that the template is readily removable after the intended cuts have been made.

BRIEF DESCRIPTION OF THE DRAWINGS

The invention will be described in detail in conjunction with the accompanying drawings, in which.

DETAILED DESCRIPTION

The invention will be initially described in connection with the various generally circular embodiments of FIGS. 1 to 8, each of which is suitably formed from initially flat sheet material in the nature of a haptic which must be very compliant in the axial direction, i.e., the axial direction through the center and normal to the plane of each of these embodiments. Such compliance enables any one of these embodiments to be self-conforming to the surface of a cornea upon wetting contact with natural fluid at the surface of the cornea. Each embodiment features elongate generally radial arms or legs having guide-slot formations which determine for the surgeon the length and spacing of cuts to be made for his particular choice of RK surgery. These arms or legs are integrally connected parts, determining what may be loosely called fenestration within an annulus for RK surgery, wherein the annulus extends outside the optical zone, namely, the central optically used circular area of the cornea.

The desired axial compliance may be suitably achieved by photographically and chemically etching an autoclavable plastic sheet material in the order of five ten-thousandths of an inch thick, wherein the material is readily available, as from the group including nylon, high-density polyethylene, Mylar[1], Teflon[1], polyethersulfone, polyester, sheet silicone, polymethylpentene, polytrichloroethylene, polyvinylidene-fluoride, and H.E.M.A, gelatin, collagen, or any of a variety of metal foils.

[1] Trademarks of the DuPont Company.

Figure 1:
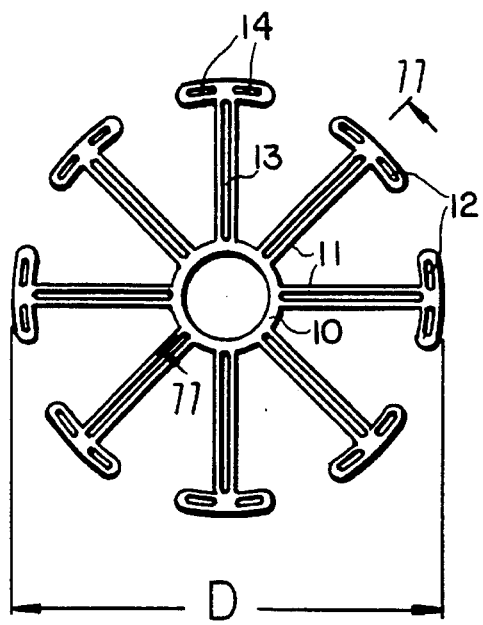
FIG. 1 is a simplified plan view of a first embodiment of a template configuration of the invention.

Turning now specifically to FIG. 1, a first template embodiment is seen to comprise a continuous circular ring 10 with plural equally spaced radial legs 11 which are terminated by short arcuate or laterally extending feet or tabs 12; tabs 12 serve to define the outer radial limit of the annulus within which an RK procedure is to be performed. Each leg II features an elongate slot 13 which is to provide guidance of the surgeon's knife; and the number and hence the spacing between legs will have been selected for the particular RK procedure. Illustratively, the inside diameter of the central ring 10 is 2.5 to 5-mm, and the outside diameter of outer ring 20 is 12.0 to 13.0-mm; the width of slots 13 may be 0.15-mm; the width of each leg 11 may be 1.0 to 2.0-mm; and the arcuate angle subtended by the outer tab feet 12 of each leg is selected such that when centered on the optical axis of the eye and conformed to the curvature of the cornea, adjacent arcuate limits of confronting tab ends are closely spaced such that surface tension of the natural moisture by which the template adheres to the cornea is operative to maintain substantially uniform spacing of all of the legs II. As shown, additional short slits or slots 14 in the respective tab feet 12, provide a means of utilizing capillary action for natural moisture of the corneal surface to enhance the adherence of outer reaches of the template to the cornea.

Once draped over in conformed adherence to the corneal curvature throughout the indicated annulus of an RK procedure, it would of course be possible for the surgeon to use an outer edge of each leg 11 as a guide for his knife manipulation, in which case the slots 13 would not be necessary. On the other hand, it is preferred that the knife-guiding slots 13 be used, particularly for the case of footplate-equipped micrometer knives of the character indicated above. These knives may be 200-microns thick or 100-microns thick, depending upon the selected "standard" or "ultra-thin" variety; in either event, the indicated guide-slot width of 0.25-mm will afford good footplate support on both lateral sides of a knife which projects through the thickness of the template in the course of making each surgical cut. Once all radial cuts have been made, the template may be lifted, as by tweezer manipulation or moisturizing.

Figure 2:
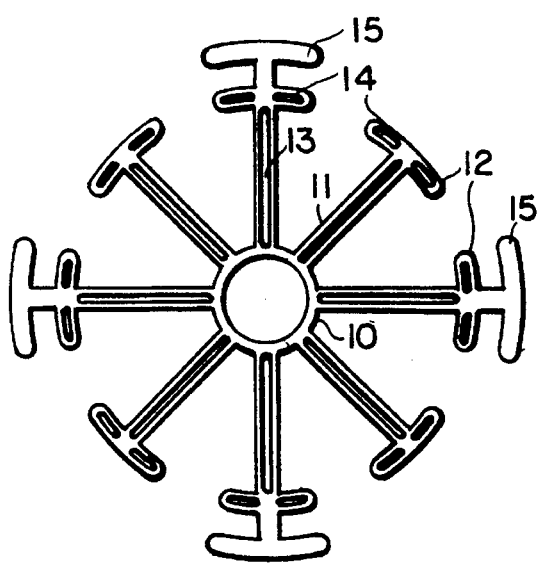
FIG. 2 is a similar view of the template of FIG. 1 having an additional feature.

The modification of FIG. 2 is identical to the described structure of FIG. 1, except for the fact that outer T-shaped tab extensions 15 are integral formations with some but not all of the legs 11. These T-shaped formations will be understood to be at such incrementally greater outer radius beyond the annulus of surgical procedure as to enable their placement under the patient's eyelids, for greater stabilization of the involved template.

Figure 3:
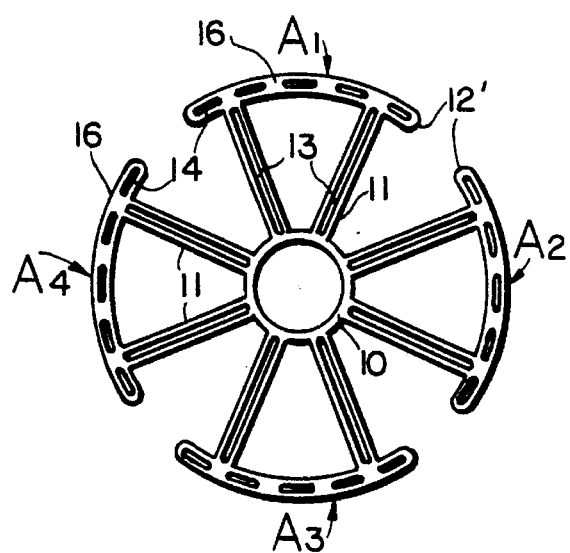
FIG. 3 is a view similar to FIG. 1, to show a first modification.

In the embodiment of FIG. 3, the central ring 10, and plural equally spaced legs 22 with their knife-guiding slots 13 are again as described for FIG. 1, but in FIG. 3 adjacent pairs of legs 11 are interconnected by outer arcs to define successive sector-shaped frames $A_1$, $A_2$, $A_3$, $A_4$ which, for the case of eight legs, establishes the sector frames in paired diametric opposition. Each of the arc connections 16 has a projecting tab end 12', and the angular space between confronting adjacent tab ends 12' is such that when the respective sector frames A, B, C, D have been draped into conformance with corneal curvature, at least a small angular clearance exists between adjacent tab ends 12'. Plural spaced arcuate slit or slot formations 14 in the arc connections 16 establish enhanced template adhesion to the cornea by reason of the capillary action mentioned above.

All of the structures of FIGS. 1 to 3 are shown for their individual planiforms in flat condition, calling for an outer circumferential shrinkage from their flat outer effective diameter D, to a lesser diameter (not shown) that is dependent upon the corneal curvature to be altered by the RK surgery.

Figure 4:
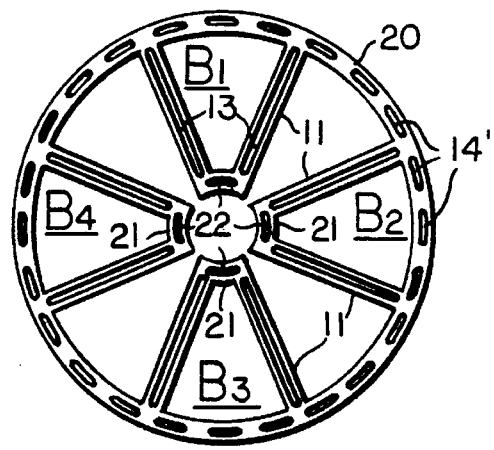
FIG. 4 is another view similar to FIG. 1, to show a second modification.

By way of contrast, and perhaps equally as effective as the embodiment of FIG. 3, is the sector-frame planiform of FIG. 4, involving plural flexible sector frames $B_1$, $B_2$, $B_3$, $B_4$ in paired diametric opposition, but integrally interconnected via a circumferentially continuous outer ring 20 having an angularly distributed series of arcuate slits or slots 14. The radially inner ends of successive pairs of radial legs 11 are integrally connected by short arcs 21. Upon draped application to the cornea, the ring 20 will establish the outer limit of radial cuts along slots 13 of the radial legs 11, but the angular space between adjacent radially inner ends of the respective sector frames will expand as necessary in adaptation to corneal curvature. FIG. 4 illustrates that for best wetted adhesion to the cornea, the inner-arc connections 21 have capillary-action slits or slots 22.

It will be appreciated that for simpler showing, the flat planiforms of frames $A_1 \ldots A_4$ of FIG. 3 and $B_1 \ldots B_4$ of FIG. 4 appear with legs 11 at equal angular spacing and that upon draping such frames into conformance with a corneal curvature, the angular space between adjacent legs 11 of adjacent sector frames (e.g., $A_1$, $A_2$) of FIG. 3 will reduce materially while the angle between legs 11 of a given sector frame will remain the same although this angle will appear to have increased; thus, RK surgical cuts made with a cornea-mounted template pursuant strictly to FIG. 3 will involve "radial" incisions that are neither purely radial nor at equal angular spacing. However, it will be further appreciated that legs 11 in FIG. 3 can readily be designed at such departures from purely radial orientation and from purely equal angular spacings as to provide purely radial knife-guidance slots 13 at equal angular spacing when in draped conformance to a given corneal curvature.

What has just been said for the legs 11 of sectors $A_1 \ldots A_4$ of FIG. 3 applies also for the legs 11 of sectors $B_1 \ldots B_4$ of FIG. 4. In other words, application of the template of FIG. 4 to an eye will spread or open up the angular clearance between inner connected ends of adjacent sector frames, thus establishing knife-guiding slots 13 that are neither strictly radial nor at equal angular spacing. However, legs 11 in FIG. 4 can readily be designed at such departures from purely radial orientation and from equal angular spacings as to provide purely radial knife-guiding slits or slots 13 at equal angular spacing when in draped conformance to a given corneal curvature.

Figure 5:
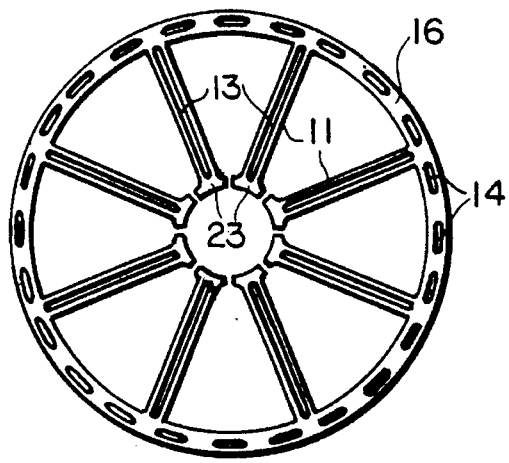
FIG. 5 is a view similar to FIG. 1, for a third modification.

In the template configuration of FIG. 5, an outer ring 16 is again circumferentially continuous but all radial legs 11 extend integrally and independently in the radially inward direction, there being no radially inner interconnection between adjacent legs 11. Thus, the inner circle around the optic zone of the cornea is a broken circle of spaced individual arcuate elements 23.

Figure 6:
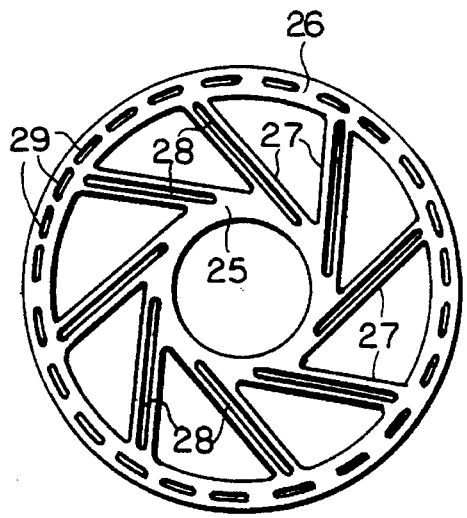
FIG. 6 is another similar view, for a fourth modification.

In the embodiment of FIG. 6, both an inner circular element 25 and an outer circular element 26 are circumferentially continuous and are integrally joined by legs 27 which are substantially tangent to equally spaced points on the inner circular element 25. Knife-guidance slots 28 extend straight and along the midsection of each leg 27. Slot-width and leg width proportions and dimensions may be otherwise as described above for strictly radial template configurations. And a preference is indicated that plural spaced capillary-action slots or slits 29 be distributed along the circumferential extent of outer circular element 26. For the flat planiform of FIG. 6, the outer circular element 26 must be draped to a corneal curvature which places element 26 in essentially a plane which is axially inward of the plane to which the inner circular element 25 is adhered. That being the case, legs 27 are caused to develop a somewhat helically arcuate appearance, as viewed from the aspect depicted in FIG. 6, i.e., as viewed along the optical axis of the eye, to which axis the template of FIG. 6 will have been concentrically applied.

Figure 7:
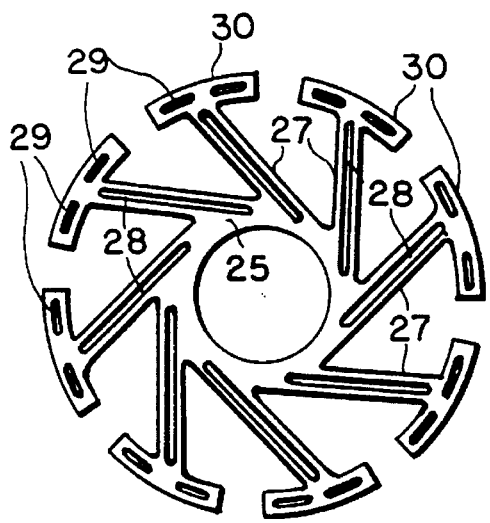
FIG. 7 is still another similar view, for a fifth modification.

In the embodiment of FIG. 7, the outer circular element 26 of FIG. 6 has been replaced by like discrete arcuate foot elements 30, each pair of elements 30 being integrally formed at the outer radial end of each leg 27. The leg (27) relation of tangency to the inner circumferentially continuous inner element 25 remains as in FIG. 6, and capillary-action slots or slits 29 are provided in each of the foot elements 30, analogous to the foot elements 12 of FIG. 1, and for the identical purpose. It is preferred that the flat planiform of FIG. 7 shall provide such angular space between adjacent ends of adjacent foot elements that, in draped condition conforming to the surface curvature of a given cornea, these adjacent ends shall be in such close proximity as, through circumferential surface-tension action between each and every gap between adjacent ends of adjacent foot elements, an equilibrium will establish itself to retain the substantially equal spacing of all legs 27.

Figure 8:
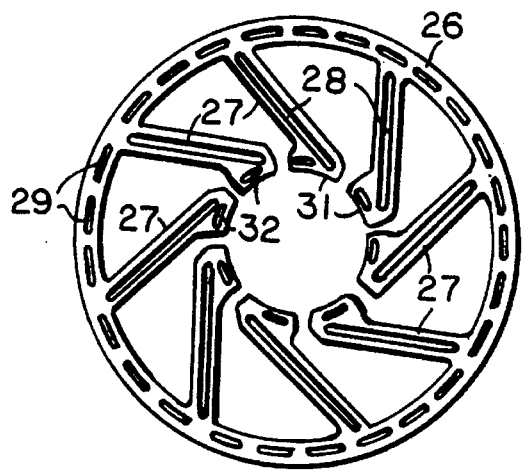
FIG. 8 is also a similar view, for a sixth modification.

As with FIG. 7, the embodiment of FIG. 8 follows the general design points of FIG. 6, except that in FIG. 8 the outer circular element 26 is circumferentially continuous and the inner circular element is discontinuous, thus forming an inner arcuate foot element 31 at the inner end of each of the potentially helical leg elements 27. As shown, a capillary-action slot or slit 32 is provided in each of the foot elements 31, and similar capillary-action slits 29 are provided in the outer circular element 26.

As an aside, it is noted with respect to the templates of FIGS. 6, 7 and 8, wherein the draped configuration results in somewhat helically arcuate courses (28) of surgical-knife invasion, the prospect exists that, as compared to RK surgery with strictly radial cuts, elastic deformation of the cornea as a result of helically arcuate incisions will engender less irregular distortion of the otherwise spherical deformation which is optimally desired for achieving an RK-derived curvature change in the optical zone of the cornea.

In the discussion thus far, it has been assumed that an RK procedure is to be performed with guidance-slot assistance such that essentially uniformly distributed incisions of uniform radial or helically arcuate extent are to be made for essentially a purely spherical correction of essentially a purely spherical myopia. With experience, however, the surgeon learns that uniform incisions (i.e., of equal length, at equal depth of corneal invasion, and at equal angular spacing) do not necessarily result in purely spherical correction, because corneas are not necessarily of the same or uniform thickness. Thus, with knowledge gained from experience, the surgeon learns that to achieve his desired optical correction, the depth of cut, and/or profiling of depth, and/or length of cut is (are) different at the respective incision locations and orientations. With such experience the described templates of FIGS. 1 to 8 will enable the surgeon to perform better patterns of incision, with greater fidelity of repeatability, not only to effect a spherical correction but also effect corrections in which astigmatism is also a factor requiring correction.

Figure 9:
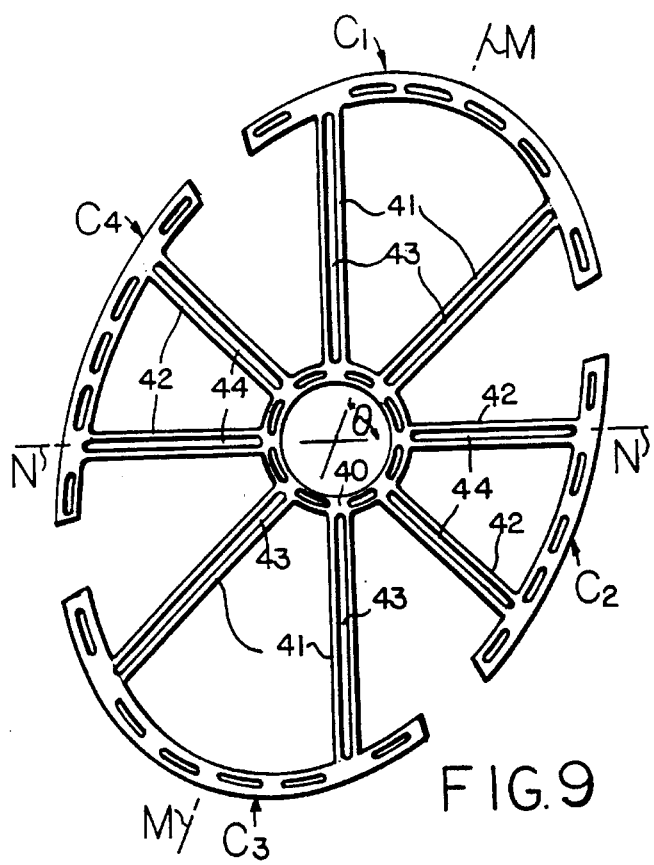
FIG. 9 is another similar view, for a seventh modification.

FIG. 9 illustrates an RK template which represents a departure from the generally circular template configurations described for FIGS. 1 to 8, in that the outer periphery is generally elliptical, for performing an astigmatic correction or a combined spherical and astigmatic correction, in which case it is of course necessary to produce such an RK pattern of cuts that cylindrical-curvature correction is effected for a particular angular orientation of diagnosed astigmatism to be effectively eliminated. Thus, in FIG. 9, the major axis M—M of the generally elliptical periphery establishes an axis of planiform symmetry and is drawn at an angle φ to the patient's natural viewing horizon N—N, merely to suggest application to a particularly diagnosed orientation of an astigmatic condition.

The illustrative planiform of FIG. 9 will be recognized as following generally the scheme of FIG. 3, except that the external periphery is elliptical. Thus, major-axis sectors $C_1$ and $C_3$ are diametrically opposed, and minor-axis sectors $C_2$ and $C_4$ are also diametrically opposed, in angularly interlaced relation with sectors $C_1$ and $C_3$. The legs all radiate from a continuous inner circle 40, and the legs 41 form parts of sectors $C_1$ and $C_3$ and are of greater length than the legs 42 of sectors $C_2$ and $C_4$. Thus, radial cuts guided by the slot formations 43 of legs 41 will be of greater extent than those guided by the slot formations 44 of legs 42. The resultant elastic deformation of a cornea which has been subjected to RK surgery based on the template of FIG. 9 will thus exhibit an elliptical distribution of local weakening, wherein both cylindrical and spherical components of curvature correction have been achieved.

Figure 10:
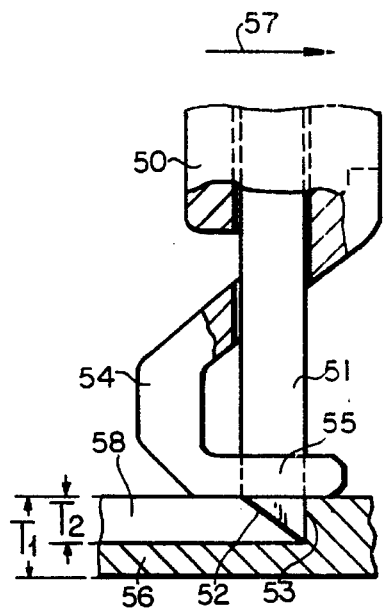
FIG. 10 is a simplified, enlarged and fragmentary view in elevation to show the distal or cutting end of a knife for use with any of the embodiments of FIGS. 1 to 9, there being additional context of the handle and footplate of the knife.

FIG. 10 is a greatly enlarged fragmentary view in side elevation for a micrometer knife of the character indicated above as representative, for use in current RK and/or AK phacorefractive surgery. The knife handle 50 will be understood to contain micrometer adjustment mechanism (not shown) for precise adjustment of the vertical positioning of a thin knife blade 51, shown with surgical cutting edges 52, 53 that are respectively vertical and at an acute angle to the vertical. Structure 54 formed with or otherwise fixed to handle 50 positions a footplate 55 for riding contact with epithelium of the anterior surface of a cornea 56, of thickness $T_1$, and in FIG. 10 knife 51 is shown in the process of left-to-right displacement (per arrow 57), using the vertical cutting edge 53 to develop a cut 58 to essentially uniform depth $T_2$. The footplate 55 will be in the nature of two like tynes or fingers, in straddling adjacency to opposite sides of blade 51. Although not shown, use of the micrometer knife of FIG. 10 will have a template leg (11, 27, 41 or 42) interposed between footplate 55 and the anterior surface of the cornea, with the cutting edge or edges of the knife passing through a guide slot (13, 28, 43 or 44). This necessarily means that for an intended cut depth $T_2$ with the invention, the cutting tip of blade 51 must be adjusted to a depth $T_2$, plus the template thickness.

Figure 11:
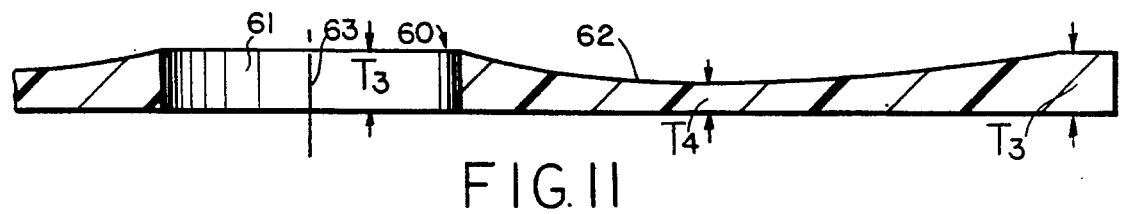
FIG. 11 is a greatly enlarged and fragmentary radial section, through a template as at 11—11 in FIG. 1, but illustrative of thickness profiling which is applicable to any of the embodiments of FIGS. 1 to 9, the section being shown for a flat condition of the template, prior to application to a cornea.

FIG. 11 illustrates that a given template 60, having an inner circular ring 61 and maximum thickness $T_3$, may be preformed to a predetermined thickness profile, here shown as a front-surface concavity 62 of thickness variation as a function of length along a leg (11, 27, 41 or 42). In other words, the concavity 62 may have uniform angular distribution about the central axis 63 of the template, so that the profile 62 characterizes all of the legs of any of the templates of FIGS. 1 to 8. On the other hand, for an elliptical configuration, or for a circular configuration that is designed to develop a component of cylindrical curvature correction, the thickness profile along some legs may be different from the thickness profile along other of the legs of the same template.

Figure 12:
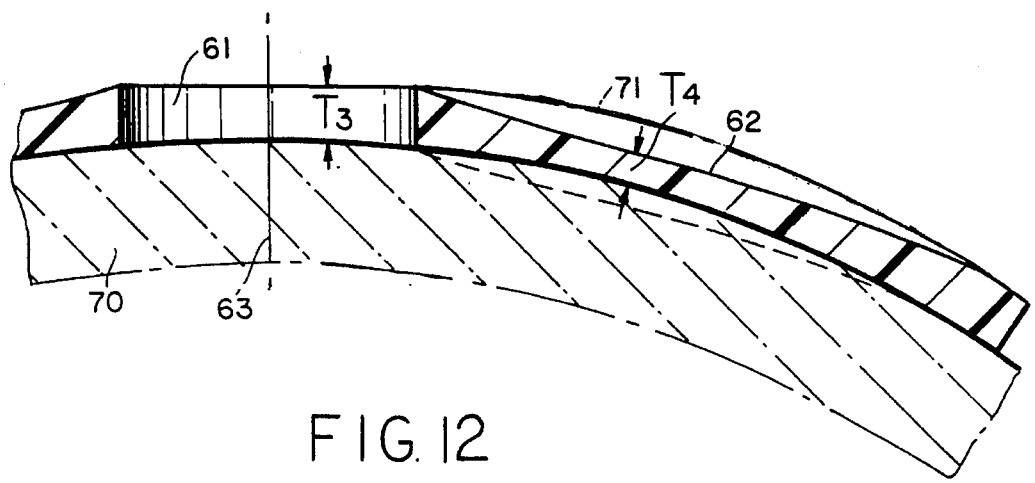
FIG. 12 is a view similar to FIG. 11, to illustrate adaptation to the curvature of the cornea, for the case of the template of FIG. 11.

FIG. 12 illustrates that in use of a thickness-profiled template, such as the template 60 of FIG. 11, the template has been draped into correctly centered positioning on and into conformance with the convex contour of a cornea 70. If template 60 had not been thickness-profiled, the front surface of the template would have determined a smoothly curved outer profile 71, in conformance with the curvature of the anterior surface of the cornea 70, and any RK cuts along guides slots (13, 28, 43 or 44) would necessarily be to uniform depth, depending upon the selected micrometer adjustment (allowing for template thickness $T_3$). However, the template profile 62, from a maximum $T_3$ to a minimum $T_4$, establishes a different appearance at the front surface 62 when template 60 has been conformed to the cornea, so that with knife 50 of FIG. 10 adjusted, for example, such that $T_2$ equals $T_3$, any guided cut in FIG. 12 will start at inner ring 61 with zero penetration into the cornea, but increasing steadily to a location of minimum template thickness but maximum cut penetration in the cornea. From here on, template 60 will determine progressively decreasing cut penetration, until at the outer end of the applicable knife-guidance slot, corneal penetration is at an end.

Figure 13:
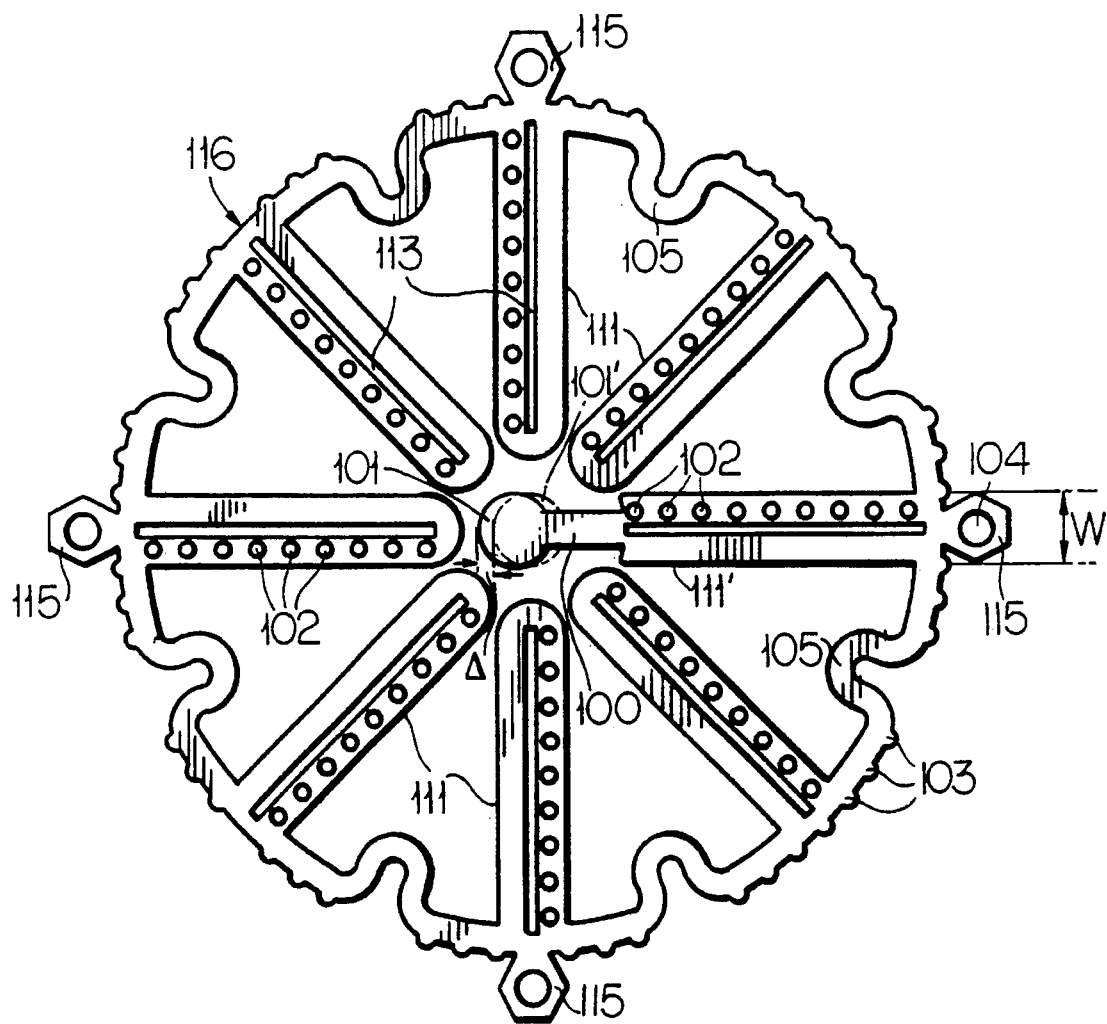
FIG. 13 is a greatly enlarged plan view of a template configuration generally analogous to that of FIG. 5 but incorporating further details which are applicable to most, if not all, of the embodiments of FIGS. 1 to 9.

The template profile of FIG. 13 has been greatly enlarged in order to identify certain features of the invention, which features will be understood to apply to most, if not all, of the embodiments of FIGS. 1 to 9, it being noted that in FIG. 13 the presently preferred general configuration of FIG. 5 has been adopted. Thus, plural radial legs 111, each with a straight knife-guidance slot 113, extend integrally and radially inward from a circumferentially continuous outer ring 116, and diametrically opposed radially outward tabs 115 provide a means of added adherence to a cornea, as by manipulated insertion beneath an eyelid.

A first feature of note in the template of FIG. 13 is that one (111') of the legs 111 is integrally formed with a further radially inward extension 100 to permit central display of a circular formation 101 which identifies the installed center of the template, as an aid to the surgeon in centering the template on a patient's cornea. It will be understood that upon placement of the template of FIG. 13 into curvature conformance with the cornea, the inner ends of legs 111 will have retracted to an extent $\Delta$ which is a function of the curvature of the cornea; that being the case the center indicium 101 of the template is shown initially formed at eccentric offset $\Delta$ from the installed central position (shown at phantom 101') in the planiform of FIG. 13. Thus, when the template has been draped into conformance with the curvature of the cornea, the indicium 101 will be truly in the center of the template, and the surgeon can manipulate the template into a truly concentric position on the patient's cornea.

A second additional feature of the template of FIG. 13 resides in provision of a precisely spaced sequence of markers, such as dots 102 (at say 0.5-mm spacings center-to-center) along each of the legs 111 and alongside the knife-guidance slot 113 of the leg. Typically, each slot 113 may be 0.15-mm wide, extending 5-mm radially inward from an outer limit at ring 116; and each leg may be of 1-mm width W. The dots 112 enable the surgeon to cut his RK or AK incisions to precisely counted radial extent, along each of the legs 111. If the depth and length of all incisions is the same, a spherical correction is achieved; and if, with experience, the surgeon wishes, he may obtain a predetermined combination of spherical and astigmatic correction by cutting to different measured extents in a given pattern of longer and shorter slot-guided incisions.

A further feature of the template of FIG. 13 resides in conspicuous angle-marking formations 103 of the continuous outer ring 116. These angle-marking formations are illustratively at 5-degree increments about the center of the template, and the surgeon is thereby enabled to use these angle-marking indicia in such orientation of the radial legs 111 as will enable performance of a procedure to achieve correction of a known astigmatic orientation in the patient's eye. The circular aperture 104 in each of the tab projections 115 provides ready access for manipulation of the template in achieving a correctly oriented position on the patient's cornea.

Another feature of the template of FIG. 13 is the fact that, although circumferentially continuous, the outer ring 116 incorporates a radially undulated formation 105 between each adjacent pair of legs 111. Such an undulation, in the context of the thin pliant nature of the template, enables virtually perfect self-conformance of the template to the epithelium of the cornea. The conformance and adhesion of the template to the corner may be even further enhanced by provision of a water-soluble adhesive on the back surface of the template. The adhesive used on postage stamps is illustrative and satisfactory because available moisture in the epithelium is sufficient, and a post-operative flushing with a balanced salt solution can provide the means of dissolving adhesive to remove the template from the patient; if water is applied to the cornea when installing an adhesively backed template, the excess moisture will aid any necessary manipulation for a particular orientation, and the excess water may be drawn off to fixate the template, prior to performing the surgery.

Still another feature of the template of FIG. 13 is that the dots 102 may be prepared as highly reflective metalized elements which, when used in conjunction with a surgical keratometer, will assist the surgeon by increasing the visibility of dots of light projected by the keratometer, as well as assisting the surgeon in his orientation of the template on the cornea. At present, i.e., without a template of the invention, the surgeon has only his dot-aligning judgment upon which to rely in use of a keratometer in connection with an RK or AK procedure; but with reflective dots 102 on a template of the invention, he has the physical guidance of slots (13, 113). An operative RK and/or AK procedure with reflective dots 102 on a template offers the prospect of making intra-operative observations of the progressive effect of the surgical procedure upon curvature changes as these changes occur, enabling the surgeon to produce improved case-to-case consistency. And the prospect is further offered for an optical and/or an electronic device (e.g., having one or more photodetector arrays) for use during RK or AK surgery to measure signals reflected from the dots, thereby giving the surgeon measurements of changing curvature data, in the course of a given procedure.

Figure 14:
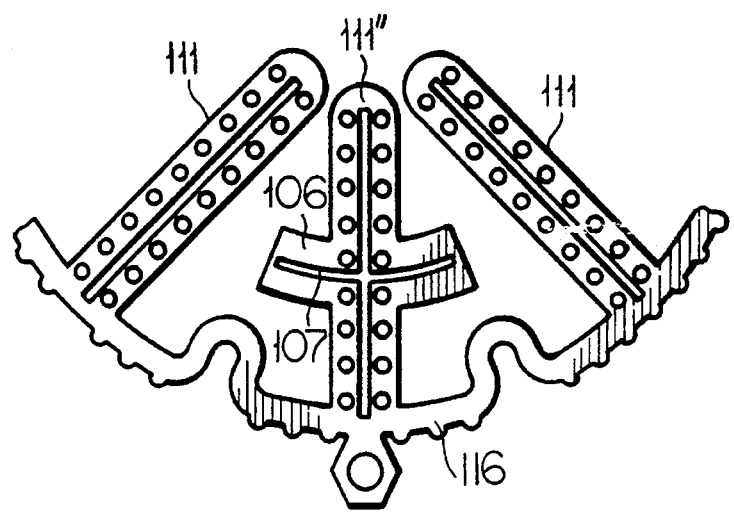
FIG. 14 is a fragmentary diagram to the scale of FIG. 13, to illustrate a modification.

The fragmentary diagram of FIG. 14 illustrates that one or more of the legs 111 of the template may be so profiled as to define a transverse arm 106 with a knife-guiding slot 107 which extends laterally of a template leg, such as the leg 111". An incision guided by such a slot (107) is consistent with a recognized pattern for astigmatic correction, and is made precisely rotatable when using a template having the knife-guidance feature of FIG. 14, once the orientation of slot 107 has been set for substantial parallelism with the diagnosed cylindrical axis of a particular patient's astigmatism. The adjusted depth of cut along slot 107, and the radial offset at which slot 107 is designed, will of course have an important bearing on the extent of astigmatic reduction. But this is a matter of the surgeon's accumulating case-to-case experience, in the course of which a template as in FIG. 14 enables consistency on a case-to-case basis.

FIG. 14 further serves to illustrate that the series of radial-distance dots 102 may be applied as like sequences on opposite sides of each radial slot (13, 113), in all described template configurations, thus presenting measurement indicia that are equally viewable either side of a given slot, as may be most convenient for any given incision.

The described template or corneal drape of the invention will be seen to have met all stated objects and to provide benefits and advantages which, in part, can be listed as follows:

1. The corneal drape or template offers an importantly enhanced reproducibility, hitherto unavailable in the practice of RK and AK surgery. This reproducibility allows repeatability of successive procedures for the individual surgeon, as well as repeatability of procedures as between one and another surgeon. It offers the prospect of providing a standard, such that other variables in the procedures can be better controlled.

2. The corneal drape or template will protect the corneal epithelium from abrasion by the foot plate of a surgical knife.

3. Presently used marking instruments and marking inks are causes of corneal abrasion and toxity in the corneal epithelium; the corneal drape or template of the invention eliminates such mechanical and chemical damage to the cornea.

4. The corneal drape or template will provide a positive stop for the knife and thus provides a level of security and precision for surgeons working with small optical zones.

The corneal drape or template also enables very precise visualization of the starting and stopping points of an incision, so that a surgeon can start and stop an incision well short of doing any damage to the knife.

5. The corneal drape or template can be designed to deal more precisely with a range of astigmatic corrections, thus reducing the extent to which "art" has hitherto been involved in such procedures. The template becomes an efficient tool for surgeons performing RK and AK procedures.

6. The corneal drape or template allows for more precise positioning over the optical center of the cornea. The surgeon can move the drape until the exact optical center is obtained, and then fixate the drape. This will reduce the amount of surgically induced astigmatism, which is currently encountered, i.e., without the invention.

7. The corneal drape or template allows for more precise intra-operative corneal topography, allowing for the surgeon's better visualization of intra-operative changes in corneal curvature.

8. The indicated manufacturing process of photographic imaging and chemical etching from thin autoclavable sheet material allows for large numbers of surgical designs to be documented and reproduced. Suitably indexed and catalogued inventories of a wide range of surgical designs offer the prospect of immediate access to and selection of the correct corneal drape or template for each individually diagnosed case requiring correction.

9. A corneal drape or template, as described, is inherently protective of a diamond knife edge. The guide slots tend to keep the knife from twisting, thereby avoiding knife-edge contact with drape or template material.

Although the templates of the present disclosure all involve eight legs having blade-guiding slot formations, this is an arbitrary although practical number, but the number 8 is not a sine qua non of the invention, in that such numbers as 6 and 4 are known to have their place in the accumulated experience data on RK procedures.

What is claimed is:

1. As an article of manufacture adapted for in-vivo self-adherent removable mounting to a cornea, an initially flat template for precision guidance of a predetermined radial keratotomy procedure, said template comprising an annular body of flexible sheet material having a central opening, said body being (1) substantially fenestrated throughout the annular area thereof and (2) of such compliant action as to deform in continuous smooth conformance to the surface curvature of a cornea and to adhere thereto solely through contact with natural moisture of the surface of a cornea, the fenestration of the annular area being characterized by plural radial slot formations of uniform knife-guiding width and at predetermined angular spacing with respect to each other.

2. The article of claim 1, in which the periphery of said annular body is a circumferentially continuous outer region and said annular body has a circumferentially continuous inner region at said central opening, said slits being radially limited by and between said regions.

3. The article of claim 1, in which said annular body is generally circular.

4. The article of claim 1, in which said annular body is generally oval.

5. As an article of manufacture adapted for in-vivo self-adherent removable mounting to a cornea, a template for precision guidance of a predetermined radial-keratotomy procedure within an annular area extending between radially inner and radially outer limits, said template comprising a body of flexible sheet material in the form of a circumferentially continuous ring defining one of the radial limits of said annular area, and plural angularly spaced elongate legs extending toward and terminating substantially at the other of said radial limits, said ring and legs being integrally connected formations of a single sheet of said material, each of said legs having a width dimension exceeding the thickness of said material and having at least one elongate knife-guiding slot formation within and at lateral offset from the respective limits of the width dimension, said legs being of such compliant nature as to deform in continuous smooth conformance to the surface curvature of a cornea and to adhere thereto through contact with natural moisture of the surface of a cornea.

6. The article of claim 5, in which said ring defines the outer limit of said annular area and said legs extend generally radially inward.

7. The article of claim 6, in which said legs extend spirally with identical angular and radial components of spiral development.

8. The article of claim 5, in which said ring defines the inner limit of said annular area and said legs extend generally radially outward.

9. The article of claim 5, in which a second ring defines the other radial limit of said annular area, and in which said legs integrally interconnect said rings.

10. The article of claim 9, in which said legs extend spirally with identical angular and radial components of spiral development.

11. The article of claim 5, wherein a distributed succession of distance-marking indicia is incorporated in each of said legs alongside each slot formation.

12. The article of claim 11, in which said marking indicia are of light-reflecting material.

13. The article of claim 12, in which said marking indicia are dots of highly reflecting material.

14. The article of claim 5, in which at least one of said legs includes a transverse arm with a knife-guiding slot that extends generally at a right angle to the involved leg.

15. The article of claim 6, in which said sheet material has at least one surface of optically reflecting nature.

16. The article of claim 6, wherein alongside each slot said body is formed with local positional indicia for tactile interpretation of length of surgical traverse under slot guidance.

17. As an article of manufacture adapted for in-vivo self-adherent removable mounting to a cornea, a template body for precision guidance of a predetermined radial keratotomy procedure within an annular area between radially inner and radially outer limits surrounding a central span of the optically used portion of the cornea, said template body comprising flexible sheet material in the form of a circumferentially continuous ring defining the radially inner limit of said annular area, and plural angularly spaced elongate legs extending outwardly of said ring, each of said legs having an elongate slot of knife-guiding width, and each of said legs terminating at said radially outer limit with like angularly directed tab formations, said tab formations having a combined effective circumferentially arcuate extent that is at least no greater than the circumferential extent of the radially outer limit of said annular area.

18. The article of claim 17, in which each of said tabs has at least one aperture, whereby to derive enhanced adherence to a cornea.

19. The article of claim 17, (i) in which said legs are of such compliant nature as to deform in continuous smooth conformance to the surface curvature of a cornea and to adhere thereto through contact with natural moisture of the surface of a cornea, and (ii) in which the combined effective circumferentially arcuate extent of said tab formations is short of the circumferential extent of the radially outer limit of said annular area, that, when deformed and adhered to the surface of a cornea, adjacent of said tabs are in such angularly spaced confronting relation that surface-tension may develop force reaction between confronting tabs of adjacent legs, to assure equal spacing of all legs.

20. As an article of manufacture adapted for in-vivo self-adherent removable mounting to a cornea, a template body for precision guidance of a predetermined radial keratotomy procedure within an annular area between radially inner and radially outer limits, said template body comprising flexible sheet material in the form of a circumferentially continuous ring defining the radially inner limit of said annular area, and an even-numbered plurality of angularly spaced elongate legs extending outwardly of said ring, each of said legs having an elongate slot of knife-guiding width, each adjacent pair of said legs terminating at said radially outward limit and an integrally formed tie interconnecting the terminal ends of the legs of each pair.

21. The method of performing a radial keratotomy procedure, which comprises selecting an initially flat template of sufficiently pliant material to drape and self-adhere to a cornea in self-adhered conformance with the surface curvature of the cornea, applying the selected template to the cornea in such self-adhered conformance, said template having pattern of RK slots, and performing the procedure with a flanged RK surgical knife having a distal cutting edge, wherein the distal cutting edge is offset beyond the flange to the extent of a predetermined depth of cut plus the template thickness.

22. The method of claim 21, in which said pattern of RK slots includes at least one slot in a template region in which template thickness varies as a predetermined function of length along at least one of said slots, whereby to develop with said knife a predetermined profile of varying depth.

23. As an article of manufacture adapted for in-vivo self-adherent removable mounting to a cornea, a template body for precision guidance of a predetermined radial keratotomy procedure within an annular area between radially inner and radially outer limits, said template body comprising flexible body sheet material in the form of a circumferentially continuous ring defining the radially outer limit of said annular area, and plural angularly spaced elongate legs extending inwardly of said ring, each of said legs having an elongate slot of knife-guiding width.

24. The article of claim 23, in which said circumferentially continuous outer ring has a radial undulation between each adjacent pair of legs.

25. The article of claim 23, in which one of said legs has a center-identifying tab formation radially inward of the radially inner limit of said annular area.

26. The article of claim 25, in which said center-identifying tab formation is circular and in which in the flattened state of said template, said center-identifying formation is centered beyond the center of said outer ring, to an extent ($\Delta$) which places said formation coaxial with a central of said outer ring when in installed and draped position in conformance with curvature of a cornea.

27. The article of claim 23, wherein said outer ring has plural marking indicia at angle-identifying increments about the periphery of said outer ring.

28. The article of claim 23, wherein said template body has a front surface and a back surface and wherein the back surface is coated with a water-soluble adhesive.

29. As an article of manufacture adapted for in-vivo self-adherent removable mounting to a cornea, a template body for precision guidance of a radial-keratotomy procedure within an annular area extending between radially inner and radially outer limits, said template body comprising flexible sheet material in the form of a circumferentially continuous ring defining one of the radial limits of said annular area and the thickness of said body being a predetermined varying function of radius with respect to said ring, and plural angularly spaced elongate legs extending toward and terminating substantially at the other of said radial limits, said ring and legs being integrally connected formations of a single sheet of said material, and each of said legs having an elongate central slot of knife-guiding width, said legs being of such compliant nature as to deform in continuous smooth conformance to the surface curvature of a cornea and to adhere thereto through contact with natural moisture of a surface of the cornea.

30. As an article of manufacture adapted for in-vivo self-adherent removable mounting to a cornea, a template for precision guidance of a predetermined radial keratotomy procedure, said template comprising an annular body of flexible sheet material having a central opening, said body being (1) substantially fenestrated throughout the annular area thereof and (2) of such compliant action as to deform in continuous smooth conformance to the surface curvature of a cornea and to adhere thereto solely through contact with natural moisture of the surface of a cornea, the fenestration of said annular area comprising angularly spaced strips which are in radially and angularly expanding spiral formations between a continuous inner-ring definition of the central opening and an continuous outer-ring definition of the periphery of said body, each of said strips being centrally slotted in conformance with the spiral formation thereof.

31. As an article of manufacture adapted for in-vivo self-adherent removable mounting to a cornea, a template for precision guidance of a predetermined radial keratotomy procedure, said template comprising an annular body of flexible sheet material having a central opening, said body being (1) substantially fenestrated throughout the annular area thereof by angularly spaced generally radial leg formations, and (2) said body being of such compliant action as to deform in continuous smooth conformance to the surface curvature of a cornea and to adhere thereto solely through contact with natural moisture of the surface of a cornea, the fenestration of the annular area being characterized by plural radial slot formations of uniform knife-guiding width in said leg formations.

* * * * *